United States Patent
Sanders et al.

(10) Patent No.: US 7,087,241 B2
(45) Date of Patent: Aug. 8, 2006

(54) COMPOSITIONS AND METHODS FOR MINIMIZING ADVERSE DRUG EXPERIENCES ASSOCIATED WITH OXYBUTYNIN THERAPY

(75) Inventors: Steven W. Sanders, Salt Lake City, UT (US); Charles D. Ebert, Salt Lake City, UT (US)

(73) Assignee: Watson Laboratories, Inc., Salt Lake City, UT (US)

( * ) Notice: Subject to any disclaimer, the term of this patent is extended or adjusted under 35 U.S.C. 154(b) by 0 days.

(21) Appl. No.: 11/246,558

(22) Filed: Oct. 7, 2005

(65) Prior Publication Data

US 2006/0078613 A1 Apr. 13, 2006

Related U.S. Application Data

(63) Continuation of application No. 10/098,752, filed on Mar. 15, 2002, now Pat. No. 6,743,441, which is a continuation of application No. 09/559,711, filed on Apr. 26, 2000, now abandoned.

(51) Int. Cl.
*A61F 13/00* (2006.01)
*A61F 13/02* (2006.01)
*A61L 15/16* (2006.01)

(52) U.S. Cl. ............ 424/449; 424/448; 424/434; 424/435; 424/422

(58) Field of Classification Search ............ 424/449, 424/448, 435, 434, 422
See application file for complete search history.

(56) References Cited

U.S. PATENT DOCUMENTS

| | | | |
|---|---|---|---|
| 4,652,441 A | 3/1987 | Okada et al. | |
| 4,959,217 A | 9/1990 | Sanders et al. | |
| 5,028,430 A | 7/1991 | Sanders et al. | |
| 5,152,997 A | 10/1992 | Ebert et al. | |
| 5,212,199 A | 5/1993 | Heiber et al. | |
| 5,227,169 A | 7/1993 | Heiber et al. | |
| 5,575,987 A | 11/1996 | Kamei et al. | |

(Continued)

FOREIGN PATENT DOCUMENTS

WO WO 92/10231 6/1992

(Continued)

OTHER PUBLICATIONS

Noronha-Blob, L. and Kachur, J.F., Enantiomers of Oxybutynin: In Vitro Pharmacological Characterization at $M_1$, $M_2$ and $M_3$ Muscarinic Receptors and in Vivo Effects on Urinary Bladder Contraction, Mydriasis and Salivary Secretion in Guinea Pigs, Journal of Pharmacology and Experimental Therapeutics, vol. 256, pp. 562-567, (1990).

(Continued)

*Primary Examiner*—Isis Ghali
(74) *Attorney, Agent, or Firm*—Thorpe North & Watson, LLP

(57) ABSTRACT

The present invention provides compositions and methods for administering oxybutynin while minimizing the incidence and or severity of adverse drug experiences associated with oxybutynin therapy. In one aspect, these compositions and methods provide a lower plasma concentration of oxybutynin metabolites, such as N-desethyloxybutynin, which is presumed to be contributing at least in part to some of the adverse drug experiences, while maintaining sufficient oxybutynin plasma concentration to benefit a subject with oxybutynin therapy. The invention also provides isomers of oxybutynin and its metabolites that meet these characteristics of minimized incidence and/or severity of adverse drug experiences, and maintenance of beneficial and effective therapy for overactive bladder.

43 Claims, 4 Drawing Sheets

U.S. PATENT DOCUMENTS

| | | | |
|---|---|---|---|
| 5,677,346 | A | 10/1997 | Aberg et al. |
| 5,759,583 | A | 6/1998 | Iwamoto et al. |
| 5,762,953 | A | 6/1998 | Venkateshwaran |
| 5,840,754 | A | 11/1998 | Guittard et al. |
| 5,922,342 | A | 7/1999 | Shah et al. |
| 5,972,369 | A | 10/1999 | Roorda et al. |
| 5,985,305 | A | 11/1999 | Peery et al. |

FOREIGN PATENT DOCUMENTS

| | | |
|---|---|---|
| WO | WO 92/20377 | 11/1992 |
| WO | WO 93/23025 | 11/1993 |
| WO | WO 95/09007 | 4/1995 |
| WO | WO 99/48493 | 9/1999 |
| WO | WO 99/48494 | 9/1999 |

OTHER PUBLICATIONS

Merritt, Ernest W. and Cooper, Eugene R., Diffusion Apparatus for Skin Penetration, Journal of controlled Release, vol. 1, pp. 161-162, (1984).

Kachur, James F. et al., "R and S Enantiomers of Oxybutynin: Pharmacological Effects in Guinea Pig Bladder and Intestine," The Journal of Pharmacology and Experimental Therapeutics, vol. 247: 3, pp. 867-872, (1988).

Johnson & Johnson 2Q EPS 89c, Dow Jones News Service, Jul. 19, 2005, pp. 1-2.

Johnson & Johnson Reports 2005 Second-Quarter Sales Increase of 11.1% and EPS of $.89 Versus $.82 a Year Ago; Excluding In-Process Research and Development Charges and Revised Tax Impact of American Jobs Creation Act, EPS Increased 13.4%, PR Newswire, Jul. 19, 2005, pp. 1-7.

Drug Delivery System, Transmucosal Film, Oxybutynin Auxilium, Phase Change I, USA, R& D Focus Drug News, UK, Jul. 18, 2005, p. 1.

Buyse, Gunnar et al., "Intravesical Oxybutynin for Neurogenic Bladder Dysfunction: Less Systemic Side Effects Due to Reduced first Pass Metabolism," The Journal of Urology, Sep. 1998, pp. 892-896, vol. 160.

Gupta, Suneel K. (PH.D) et al., "Pharmacokinetics of an Oral Once-a-Day Controlled-Release Oxybutynin Formulation Compared with Immediate-Release Oxybutynin," J. Clin. Pharmacol, 1999, pp. 289-296, vol. 39.

Patient Assessment of Symptom Severity

COMPOSITIONS AND METHODS FOR MINIMIZING ADVERSE DRUG EXPERIENCES ASSOCIATED WITH OXYBUTYNIN THERAPY

PRIORITY DATA

This patent application is a continuation of U.S. patent application Ser. No. 10/098,752, filed Mar. 15, 2002, now U.S. Pat. No. 6,743,441 which is a continuation of U.S. patent application Ser. No. 09/559,711, filed Apr. 26, 2000, now abandoned each of which are incorporated herein by reference.

FIELD OF THE INVENTION

The present invention relates to compositions and methods for minimizing adverse drug experiences associated with oxybutynin therapy. Accordingly, this invention covers the fields of pharmaceutical sciences, medicine and other health sciences.

BACKGROUND OF THE INVENTION

Oral oxybutynin is currently used for treating various forms of overactive bladder and urinary incontinence. Particularly, oxybutynin effectively treats neurogenically caused bladder disorders. Relief from such disorders is attributed to the anticholinergic and antispasmodic action which oxybutynin imparts to the parasympathetic nervous system and the urinary bladder detrusor muscle.

It is generally believed that, while this anticholinergic activity contributes to oxybutynin's clinical usefulness, it also contributes to certain uncomfortable adverse drug experiences such as dry mouth, dizziness, blurred vision, and constipation. More specifically, these experiences have been generally attributed to the presence and amount of active metabolites of oxybutynin, for example, N-desethyloxybutynin. The above-referenced adverse drug experiences are observed in a majority of patients using current oxybutynin formulations. In some cases, these adverse experiences are severe enough to persuade the patient to discontinue treatment.

In view of the foregoing, compositions and methods for administering oxybutynin to help minimize the incidence and/or severity of the above-described adverse drug experiences are extremely desirable.

SUMMARY OF THE INVENTION

Accordingly, the present invention provides a method of minimizing an adverse drug experience associated with oxybutynin therapy which comprises the step of administering a pharmaceutical composition comprising oxybutynin to a subject such that the ratio of area under the plasma concentration-time curve (AUC) of oxybutynin to an oxybutynin metabolite is about 0.5:1 to about 5:1. The adverse drug experience may be any adverse experience resulting from administration of oxybutynin, for example, anticholinergic, and/or antimuscarinic in nature.

Specific examples of known oxybutynin adverse experiences include but are not limited to: gastrointestinal/genitourinary experiences, nervous system experiences, cardiovascular experiences, dermatological experiences, and opthalmic experiences, among others.

Delivery formulations useful in conjunction with the method of the present invention include but are not limited to: oral, parenteral, transdermal, inhalant, or implantable formulations. In one aspect of the invention, the delivery formulation is a transdermal delivery formulation.

Oxybutynin has a chiral molecular center, leading to the presence of (R)- and (S)-isomers. When metabolized, oxybutynin gives rise to metabolites such as N-desethyloxybutynin, which may also be present as (R)- and (S)-isomers or a combination thereof. The method of the present invention specifically encompasses each isomer for both oxybutynin and its any corresponding metabolites. For example, in one aspect, the mean plasma AUC ratio of (R)-oxybutynin to (S)-oxybutynin is about 0.7:1. In another aspect, the mean AUC ratio of (R)-N-desethyloxybutynin to (R)-oxybutynin is from about 0.4:1 to about 1.6:1. In one aspect, this mean AUC ratio may be about 1:1. In another aspect, the mean AUC ratio of (R)-N-desethyloxybutynin to (S)-N-desethyloxybutynin is from about 0.5:1 to about 1.3:1. For example, this mean AUC ratio may be about 0.9:1. In another aspect, the metabolite may have a mean peak plasma concentration of less than about 8 ng/ml.

A pharmaceutical composition for administering oxybutynin to a subject is also provided, comprising oxybutynin that provides an AUC ratio of oxybutynin to an oxybutynin metabolite of from about 0.5:1 to about 5:1.

Examples of suitable dosage formulations for the composition include: oral, parenteral, transdermal, inhalant, or implantable type compositions. In one aspect, the composition is a transdermal composition.

The compositions may contain oxybutynin in its various (R)- and (S)-isomeric forms, or mixtures thereof. Further, the compositions may include as well as (R) and (S)-isomeric forms oxybutynin metabolites. In one aspect of the present invention, the composition results in an (R)-oxybutynin to (S)-oxybutynin mean AUC ratio of about 0.7:1. In another aspect, the composition of the present invention results in an (R)-N-desethyloxybutynin to (R)-oxybutynin mean AUC ratio of from about 0.4:1 to about 1.6:1. In an additional aspect, this ratio is about 1:1. In another aspect, the (R)-N-desethyloxybutynin to (S)-N-desethyloxybutynin mean AUC ratio may be from about 0.5:1 to about 1.3:1. In one aspect, the ratio is about 0.9:1. In yet another aspect, the mean peak metabolite plasma concentration may be less than about 8 ng/ml.

The composition of the present invention may include a pharmaceutically acceptable carrier, and other ingredients as dictated by the particular needs of the specific dosage formulation. Such ingredients are well known to those skilled in the art. See for example, Gennaro, A. *Remington: The Science and Practice of Pharmacy* 19$^{th}$ ed. (1995), which is incorporated by reference in its entirety. For example, a transdermal formulation include, but not limited to, permeation enhancers, anti-irritants, adhesion adjusters, and combinations thereof.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

DETAILED DESCRIPTION

Definitions

Figure 1:
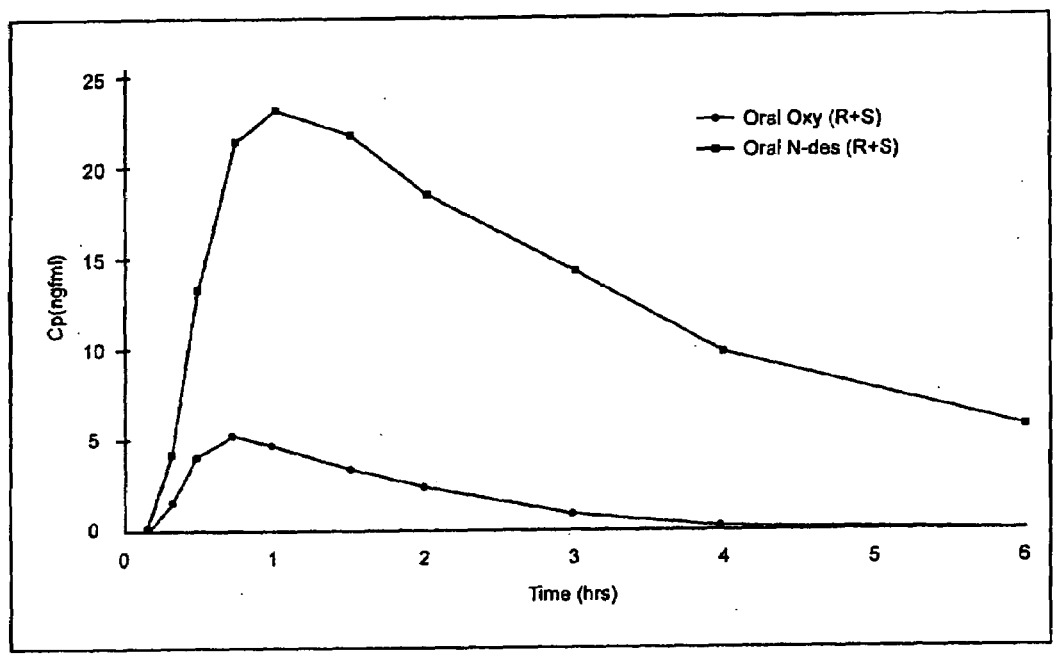
FIG. 1 is a graphical representation of total oxybutynin and N-desethyloxybutynin plasma concentrations measured following a 5 mg oxybutynin immediate-release oral dosage formulation.
Figure 2:
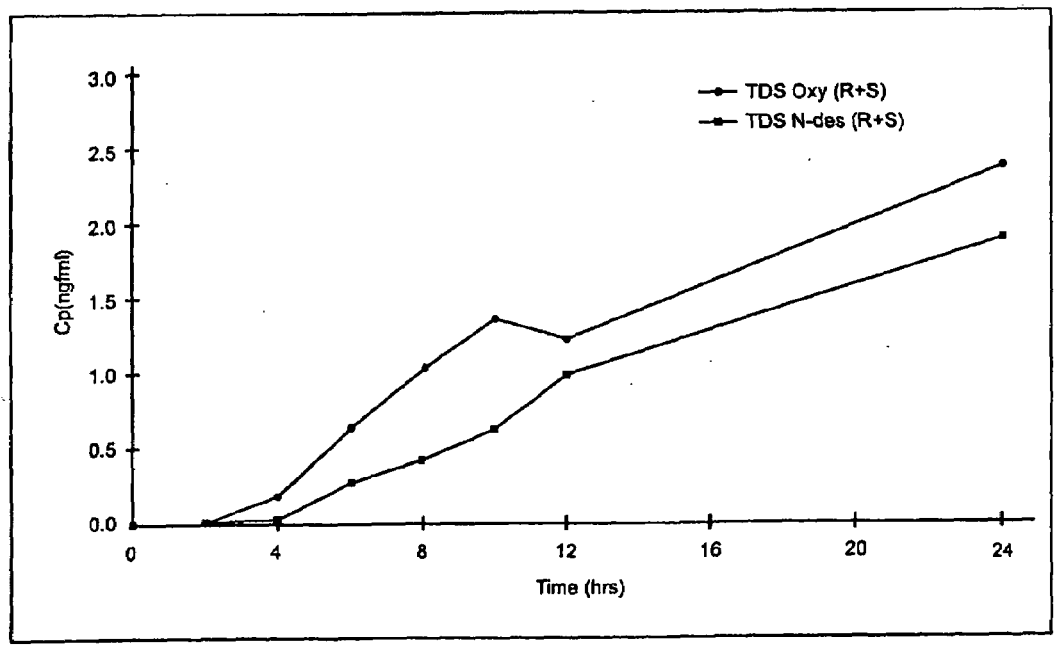
FIG. 2 is a graphical representation of total oxybutynin and N-desethyloxybutynin plasma concentrations measured upon transdermal administration according to the present invention, spanning a time from initial oxybutynin administration to 24 hours therefrom.

In describing and claiming the present invention, the following terminology will be used in accordance with the definitions set forth below.

The singular forms "a," "an," and, "the" include plural referents unless the context clearly dictates otherwise. Thus, for example, reference to "an adhesive" includes reference to one or more of such adhesives, and reference to "an excipient" includes reference to one or more of such excipients.

"Oxybutynin" refers to the compound known by several IUPAC names such as α-Cyclohexyl-α-hydroxy-benzenacetic acid 4-(diethylamino)-2-butynyl ester; α-phenylcyclohexaneglycolic acid 4-(diethylamino)-2-butynyl ester; and 4-diethylamino-2-butynylphenylcyclohexylglycolate. The oxybutynin acid addition salt, oxybutynin HCl, is listed in the Merck Index, entry no., 7089, at page 1193, 12th ed., (1996). "Oxybutynin" as used herein includes oxybutynin free base, its acid addition salts such as oxybutynin HCl, their analogs and related compounds, isomers, polymorphs, and prodrugs thereof. It is generally known that oxybutynin may exist in one or both of its isomeric forms, known as the (R)- and (S)-isomers, or a mixture of these two isomers. These isomeric forms and their mixtures are within the scope of this invention.

"Administration," and "administering" refer to the manner in which a drug is presented to a subject. Administration can be accomplished by various art-known routes such as oral, parenteral, transdermal, inhalation, implantation, etc. Thus, an oral administration can be achieved by swallowing, chewing, sucking of an oral dosage form comprising the drug. Parenteral administration can be achieved by injecting a drug composition intravenously, intra-arterially, intramuscularly, intrathecally, or subcutaneously, etc. Transdermal administration can be accomplished by applying, pasting, rolling, attaching, pouring, pressing, rubbing, etc., of a transdermal preparation onto a skin surface. These and additional methods of administration are well-known in the art.

The term "non-oral administration" represents any method of administration in which a drug composition is not provided in a solid or liquid oral dosage form, wherein such solid or liquid oral dosage form is traditionally intended to substantially release and or deliver the drug in the gastrointestinal tract beyond the mouth and/or buccal cavity. Such solid dosage forms include conventional tablets, capsules, caplets, etc., which do not substantially release the drug in the mouth or in the oral cavity.

It is appreciated that many oral liquid dosage forms such as solutions, suspensions, emulsions, etc., and some oral solid dosage forms may release some of the drug in the mouth or in the oral cavity during the swallowing of these formulations. However, due to their very short transit time through the mouth and the oral cavities, the release of drug from these formulations in the mouth or the oral cavity is considered de minimus or insubstantial. Thus, buccal patches, adhesive films, sublingual tablets, and lozenges that are designed to release the drug in the mouth are non-oral compositions for the present purposes.

In addition, it is understood that the term "non-oral" includes parenteral, transdermal, inhalation, implant, and vaginal or rectal formulations and administrations. Further, implant formulations are to be included in the term "non-oral," regardless of the physical location of implantation. Particularly, implantation formulations are known which are specifically designed for implantation and retention in the gastrointestinal tract. Such implants are also considered to be non-oral delivery formulations, and therefore are encompassed by the term "non-oral."

The term "subject" refers to a mammal that may benefit from the administration of a drug composition or method of this invention. Examples of subjects include humans, and other animals such as horses, pigs, cattle, dogs, cats, rabbits, and aquatic mammals.

As used herein, the terms "formulation" and "composition" are used interchangeably. The terms "drug" and "pharmaceutical" are also used interchangeably to refer to a pharmacologically active substance or composition. These terms of art are well-known in the pharmaceutical and medicinal arts.

The term "transdermal" refers to the route of administration that facilitates transfer of a drug through a skin surface wherein a transdermal composition is administered to the skin surface.

The term "skin" or "skin surface" is meant to include not only the outer skin of a subject comprising one or more of epidermal layers, but also to include mucosal surfaces to which a drug composition may be administered. Examples of mucosal surfaces include the mucosa of the respiratory (including nasal and pulmonary), oral (mouth and buccal), vaginal, and rectal cavities. Hence the terms "transdermal" may encompass "transmucosal" as well.

The terms "enhancement", or "permeation enhancement," mean an increase in the permeability of the skin, to a drug, so as to increase the rate at which the drug permeates through the skin. Thus, "permeation enhancer" or simply "enhancer" refers to an agent, or mixture of agents that achieves such permeation enhancement.

An "effective amount" of an enhancer means an amount effective to increase penetration of a drug through the skin, to a selected degree. Methods for assaying the characteristics of permeation enhancers are well-known in the art. See, for example, Merritt et al., Diffusion Apparatus for Skin Penetration, *J. of Controlled Release* 61 (1984), incorporated herein by reference in its entirety. By "effective amount" or "therapeutically effective amount," or similar terms is meant a non-toxic but sufficient amount of a drug, to achieve therapeutic results in treating a condition for which the drug is known to be effective. The determination of an effective amount is well-within the ordinary skill in the art of pharmaceutical and medical sciences. See for example, Curtis L. Meinert & Susan Tonascia, *Clinical Trials: Design, Conduct, and Analysis*, Monographs in Epidemiology and Biostatistics, vol. 8 (1986).

By the term "mean," "mathematical mean," "average," or similar terms when used in conjunction with the recitation of a number, or numbers, means the sum of all the individual observations or items of a sample divided by the number of items in the sample.

By the term "matrix", "matrix system", or "matrix patch" is meant a composition comprising an effective amount of a drug dissolved or dispersed in a polymeric phase, which may also contain other ingredients, such as a permeation enhancer and other optional ingredients. This definition is meant to include embodiments wherein such polymeric phase is laminated to a pressure sensitive adhesive or used within an overlay adhesive.

A matrix system may also comprise an adhesive layer having an impermeable film backing attached onto the distal surface thereof and, before transdermal application, a release liner on the proximal surface of the adhesive. The film backing protects the polymeric phase of the matrix patch and prevents release of the drug and/or optional ingredients to the environment. The release liner functions similarly to the impermeable backing, but is removed from the matrix patch prior to application of the patch to the skin as defined above. Matrix patches with the above-described general characteristics are known in the art of transdermal delivery. See, for example, U.S. Pat. Nos. 5,985,317, 5,783,208, 5,626,866, 5,227,169, which are incorporated by reference in their entirety.

"Topical formulation" means a composition in which the drug may be placed for direct application to a skin surface and from which an effective amount of the drug is released.

"Adverse drug experience" refers to any adverse event associated with the use of a drug in a subject, including the following: an adverse event occurring in the course of the use of a drug product in professional practice; an adverse event occurring from drug overdose whether accidental or intentional; an adverse event occurring from drug abuse; an adverse event occurring from drug withdrawal; and any failure of expected pharmacological action. The adverse drug experience may lead to a substantial disruption of a person's ability to conduct normal life functions. In some instances, the adverse drug experience may be serious or life threatening.

While some of the adverse drug experiences may be expected, in some instances, such experiences may be unexpected. "Unexpected," refers to an adverse drug experience that has not been previously catalogued by a responsible governmental agency (such as the Food and Drug Administration of the United States) and or not provided in the current labeling for the drug product.

The unexpected adverse experiences may include events that may be symptomatically and pathophysiologically related to a known event, but differ from the event because of greater severity or specificity. For example, under this definition, hepatic necrosis would be unexpected (by virtue of greater severity) if the known event is elevated hepatic enzymes or hepatitis. Similarly, cerebral thromboembolism and cerebral vasculitis would be unexpected (by virtue of greater specificity) if the known event is cerebral vascular accidents. For a more comprehensive definition and description of adverse drug experience, see 21 C.F.R. § 314.80, which is incorporated by reference in its entirety.

The majority of the adverse experiences associated with oxybutynin therapy may be categorized as anticholinergic, and/or antimuscarinic. Certain adverse experiences associated with oxybutynin have been categorized in the Physician's Desk Reference as cardiovascular experiences, gastrointestinal/genitourinary experiences, dermatologic experiences, nervous system experiences, and opthalmic experiences, among others.

Examples of cardiovascular adverse experiences include but are not limited to: palpitations, tachycardia, vasodilation, and combinations thereof. Examples of dermatologic adverse experiences include but are not limited to: decreased sweating, rashes, and combinations thereof. Examples of gastrointestinal/genitourinary adverse experiences include but are not limited to: constipation, decreased gastrointestinal motility, dry mouth, nausea, urinary hesitance and retention, and combinations thereof. Examples of nervous system adverse experiences include but are not limited to: asthenia, dizziness, drowsiness, hallucinations, insomnia, restlessness, and combinations thereof. Examples of opthalmic adverse experiences include but are not limited to: amblyopia, cycloplegia, decreased lacrimation, mydriasis, and combinations thereof. Examples of other adverse experiences include but are not limited to: impotence and suppression of lactation. A more comprehensive listing of adverse experiences my be found in the labeling of the oxybutynin formulations as provided by the regulatory agencies.

The term "minimize" and its grammatical equivalents refer to a reduction in the frequency and or severity of one or more adverse drug experiences in a given subject or subject population. It is appreciated that the subject population may be of necessity much smaller in size than the general population that may be exposed to the drug and/or its adverse experiences.

It is also appreciated that the results obtained from methods for determining the reduction in the frequency and/or severity of adverse drug experiences may be subject to variables such as intra-subject and inter-subject factors. However, it is also appreciated that certain scientifically accepted methods can be used to conduct the studies and that the results from such studies are statistically reliable. Such methods and interpretation of the results from such methods are well-known in the art. See, for example, Robert R. Sokal & F. James Rohlf, *Biometry: The Principles and Practice of Statistics in Biological Research*, $2^{nd}$ ed. (1969), which is incorporated by reference in its entirety.

The phrase "area under the curve", "area under the plasma concentration-time curve," or similar terms are well known in the pharmaceutical arts. These values are calculated by plotting a graph with data from plasma concentration of a given drug or its metabolites as a function of time, with the X-axis generally representing time and the Y-axis generally representing plasma concentration. The area under the line formed by joining the various data points is then integrated into a numerical value. See for example, Milo Gibaldi & Donald Perrier, *PharmacoKinetics*, $2^{nd}$ ed. (1982). The AUC multiplied by the clearance or total body clearance (CL), of the substance being measured, thus provides an estimate of the total amount, or dose, of the substance being measured (the drug or one or more of its metabolites). Plasma concentrations, AUC, and CL may be subject to inter- and intra-subject variation due to physiological and/or environment factors present in individual subjects during the administration of medicinal agents, such as oxybutynin, in various formulation and/or compositions. Therefore, individual and mean values may be subject to variability, however, the general trends and relationships are preserved and reproducible.

Concentrations, amounts, solubilities, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

For example, a concentration range of 0.1 to 5 ng/ml should be interpreted to include not only the explicitly recited concentration limits of 0.1 ng/ml and 5 ng/ml, but also to include individual concentrations such as 0.2 ng/ml, 0.7 ng/ml, 1.0 ng/ml, 2.2 ng/ml, 3.6 ng/ml, 4.2 ng/ml, and sub-ranges such as 0.3–2.5 ng/ml, 1.8–3.2 ng/ml, 2.6–4.9 ng/ml, etc. This interpretation should apply regardless of the breadth of the range or the characteristic being described.

The Invention

As described above, the present invention provides compositions and methods for administering oxybutynin. These compositions and methods are shown to have minimized the incidence and/or severity of an adverse experience associated with oxybutynin administration, while providing sufficient oxybutynin to impart a therapeutic benefit. Without intending to be bound to any specific theory, it is believed that the minimization of adverse experiences is due in part to the reduction in plasma concentration of metabolites of oxybutynin such as N-desethyloxybutynin by the present compositions and methods when compared to conventional oral administration. The phrase "conventional oral administration" is meant to include the oral formulations as defined supra, and includes for example, an immediate-release or sustained-release oral tablet comprising oxybutynin. One such conventional oral formulation is available as a 5 mg immediate-release oral tablet.

1) The Pharmacokinetic Aspects Associated with Total Drug and Metabolite Plasma Concentrations The desired pharmacokinetic attributes such as reduced plasma concentrations of oxybutynin metabolites may be achieved by, inter alia: 1) reducing the amount of oxybutynin administered, 2) reducing the rate at which oxybutynin becomes available for metabolism by the body, and/or 3) avoiding or minimizing first-pass hepatic and/or intestinal metabolism of oxybutynin. Using a non-oral route of administration is one way to achieve one or more of these objectives. Alternatively, an oral dosage form could be designed to mimic a non-oral administration to achieve the plasma concentrations and other pharmacokinetic data described herein.

A clinical study has been performed to demonstrate one embodiment of the present invention. A cross-over clinical study in 16 healthy volunteers was conducted to compare plasma concentrations and pharmacokinetics of oxybutynin and one of its metabolites, N-desethyloxybutynin, and their respective (R)- and (S)-enantiomeric components.

Conventional oral dosage forms of oxybutynin, such as the 5 mg oxybutynin tablet used in the present study produce significantly higher plasma concentrations of oxybutynin metabolites such as N-desethyloxybutynin as compared to the parent drug. (See FIG. 1). The mean AUC ratio of metabolite to oxybutynin concentration is about 10:1 in the majority of cases, and is generally greater than about 5:1.

In contrast, when oxybutynin is administered in a non-oral, slow release composition, such as the transdermal composition embodiment of the present invention, the mean AUC ratio of the metabolite (N-desethyloxybutynin) to oxybutynin is much lower. Generally, the mean AUC ratio of oxybutynin metabolite (N-desethyloxybutynin) to oxybutynin is less than about 2:1. Further, in the majority of instances, the ratio is less than about 1.2:1, and often, the ratio is approximately 0.9:1. (See FIG. 3).

Additionally, the mean N-desethyloxybutynin plasma concentration is generally less than about 8 ng/ml, and in the majority of instances is less than about 5 ng/ml. Often the mean is less than about 3 ng/ml.

2) Pharmacokinetic Aspects of Isomers

The present inventors have investigated further into the aspects described above and have discovered that the present formulations and methods provide significantly reduced levels of particular isomers of certain oxybutynin metabolites and that these reduced levels of metabolite isomers correlate to the minimized adverse drug experiences described above.

It is generally known that oxybutynin exists as an (R)- or as an (S)-isomer or a combination thereof. Particularly, (R)-oxybutynin has been thought to be the more active of the two isomers, as indicated by animal pharmacological studies using isolated tissues. See for example, Kachur J F, Peterson J S, Carter J P, et al. *J. Pharm Exper. Ther.* 1988; 247: 867–872; see also, Noronha-Blob L, Kachur J F. *J. Pharm. Exper. Ther.* 1990; 256:56–567. As such, (R)-N-desethyloxybutynin, being the more active constituent of the total amount of metabolite, may contribute more significantly to adverse drug experiences such as anticholinergic adverse effects than the less active(S)-N-desethyloxybutynin. See for example, U.S. Pat. No. 5,677,346, which is incorporated by reference in its entirety.

Accordingly, plasma concentrations were measured for both (R)- and (S)-oxybutynin and the corresponding isomers of one of its metabolites, N-desethyloxybutynin during the clinical study mentioned above. The tests performed revealed that the present invention results in significantly lower (R)-N-desethyloxybutynin plasma concentrations compared to conventional oral dosage forms and administration methods.

Figure 6:
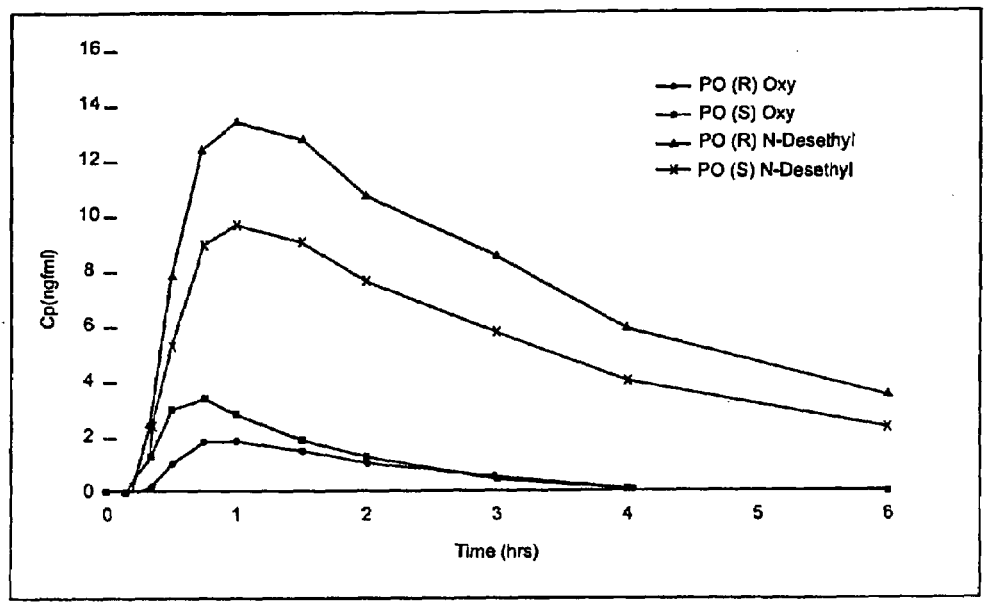
FIG. 6 is a graphical representation of the plasma concentrations produced for the (R) and (S) isomers of both oxybutynin and N-desethyloxybutynin upon administering a 5 mg immediate-release oral tablet.

FIG. 6 shows the plasma concentration profile from the conventional oxybutynin 5 mg oxybutynin oral tablet. As can be seen, (R)-N-desethyloxybutynin is present in the greatest concentration, and is several times the concentration of both (R)- and (S)-oxybutynin. The mean AUC ratio of the (R)-N-desethyloxybutynin to (R)-oxybutynin, the two most active isomers, following oral administration is about 17:1. In addition, the mean AUC ratio of (R)-N-desethyloxybutynin to (S)-N-desethyloxybutynin is about 1.5:1, and the mean AUC ratio of (R)-oxybutynin to (S)-oxybutynin is about 0.6:1. These ratios of AUC consistently show that orally administered oxybutynin results in a relatively low amount of therapeutically active (R)-oxybutynin given the large total dose of racemic oxybutynin. Further, the oral dose results in a relatively large amount of (R)-N-desethyloxybutynin, the moiety most likely to be responsible for causing some or many of the adverse drug experiences.

Figure 7:
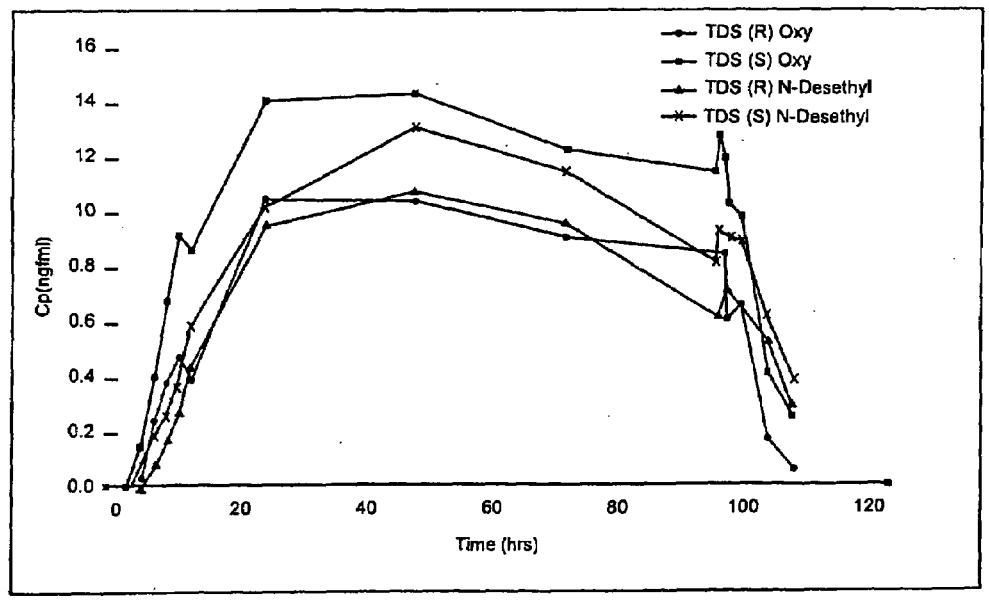
FIG. 7 is a graphical representation of the plasma concentrations of (R) and (S) isomers for both oxybutynin and N-desethyloxybutynin achieved by transdermal administration in accordance with the present invention.

In contrast, FIG. 7 shows the (R)- and (S)-isomer plasma profiles of the present invention which were achieved during the clinical study by non-orally delivered oxybutynin. The mean AUC ratio of (R)-oxybutynin to (S)-oxybutynin is about 0.7:1, and the sustained plasma concentrations of (R)-oxybutynin are similar to the peak concentrations obtained following oral administration. This comparable exposure to the therapeutically active (R)-oxybutynin moiety is consistent with the invention.

Thus, with transdermal administration, it has been discovered that: the mean AUC ratio of (R)-N-desethyloxybutynin to (R)-oxybutynin is lowered, resulting in greatly reduced amounts of the active metabolites of oxybutynin, while providing a therapeutically effective amount of oxybutynin.

Figure 4:
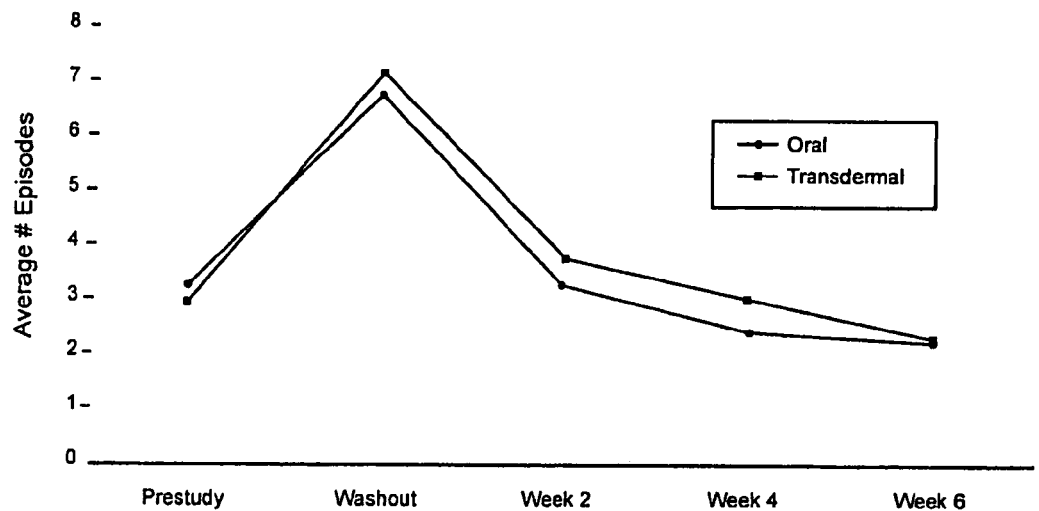
FIG. 4 is a graphical representation of the results of treating a subject with overactive bladder with transdermal administration of oxybutynin in accordance with the present invention, as compared to treatment with a 5 mg immediate-release oxybutynin oral tablet by recording the number of episodes of urinary incontinence.
Figure 5:
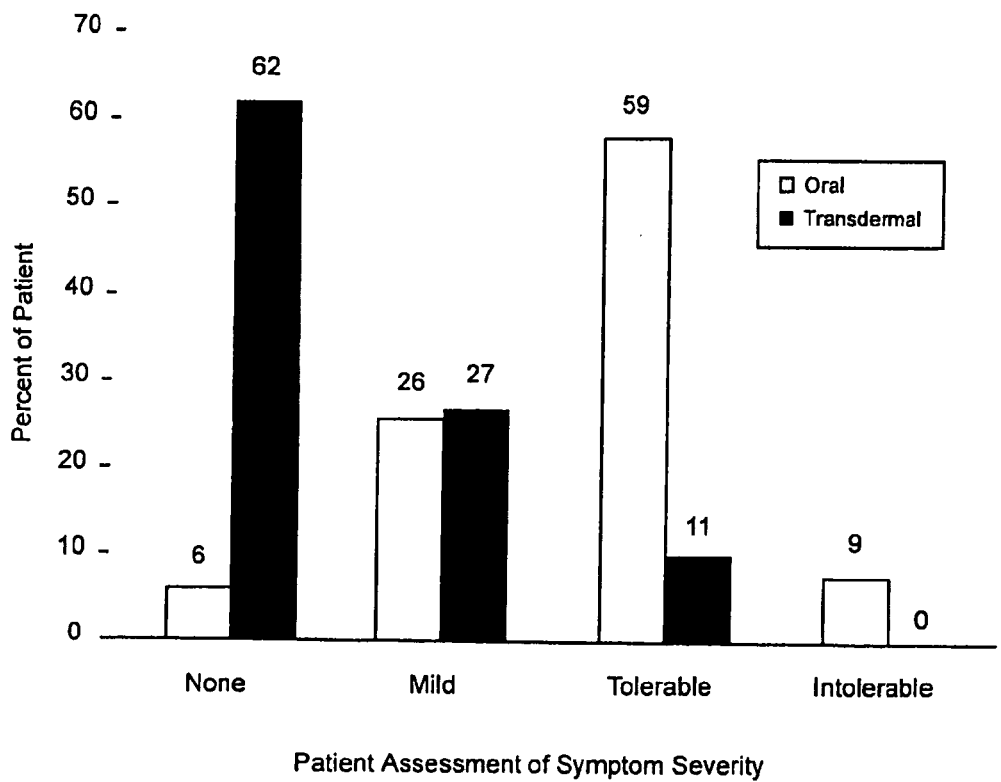
FIG. 5 is a graphical representation of the anticholinergic adverse experiences reported by subjects receiving treatment for overactive bladder with a transdermal administration of oxybutynin in accordance with the present invention, as compared to treatment with a 5 mg oxybutynin immediate-release oral tablet.

By comparing FIGS. 4, 5, and 7, it becomes clear that the present compositions and methods provide an optimal ratio of plasma concentrations of metabolites, such as (R)-N-desethyloxybutynin, to oxybutynin, such that these methods and compositions minimize adverse experiences associated with oxybutynin administration, as compared to traditional oral formulations, while maintaining therapeutically sufficient concentrations of (R)-oxybutynin to provide the benefits of oxybutynin therapy. As indicated above, these compositions and methods offer a significant advancement in oxybutynin therapy.

3) Therapeutic Aspects

A clinical study on the efficacy and minimization of incidence and severity of adverse drug experiences associated with non-orally administered oxybutynin was conducted using 72 human subjects (patients) with overactive bladder. Approximately one-half of the patients were administered oxybutynin hydrochloride in an oral dosage formulation. The remaining patients were administered oxybutynin using a non-oral route of delivery such as a transdermal adhesive matrix patch over a period of about 6 weeks. The results are displayed graphically in FIGS. 4 and 5.

The non-oral, sustained-release composition of this invention was compared for its therapeutic efficacy with the conventional 5 mg oral tablet of oxybutynin. The mean number of incontinent episodes experienced per day as derived from a multiple-day patient urinary diary was used as the desired therapeutic efficacy indicator. The data show that the number of incontinent episodes for those individuals treated by the non-oral method of the present invention is nearly identical to the number for those treated with the oral formulation. (See FIG. 4).

Next, the non-oral sustained-release formulation of the present invention was compared to the conventional immediate-release oral tablet for the incidence and severity of adverse drug experiences. The adverse experience of dry mouth was selected as an indicator for this experiment. As can be seen, only 6% of the participants who received the conventional oral oxybutynin tablet reported no dry mouth effects. Conversely, 94% of these participants reported experiencing some dry mouth.

In contrast, 62% of the participants who were treated with the transdermal adhesive matrix patch of the present invention reported no dry mouth effects. Therefore, only 38% of these participants reported experiencing some dry mouth, and none rated the dry mouth as intolerable.

These data show that the adverse experiences associated with oxybutynin administration can be minimized significantly, while fully retaining the therapeutic efficacy of oxybutynin by administering oxybutynin such that an optimal ratio of AUC of oxybutynin metabolite to oxybutynin results.

4) Summary of Pharmacokinetic Aspects of the Invention

From the above-described pharmacokinetic data, the following aspects of the invention can be presented. In one aspect, the mean peak plasma concentration of an oxybutynin metabolite is less than about 8 ng/ml. In another aspect, the mean peak plasma concentration of the metabolite is from about 0.5 ng/ml to about 8 ng/ml; in yet another aspect, the concentration is less than about 5 ng/ml; in yet another aspect, the concentration is from about 1.0 ng/ml to about 3 ng/ml. In some aspects, the metabolite of oxybutynin is N-desethyloxybutynin.

In some aspects, the mean oxybutynin metabolite AUC is reduced to an amount which does not exceed the oxybutynin AUC by more than a ratio of about 2:1. In some aspects, the mean oxybutynin metabolite AUC is reduced to less than about 0.9:1 ng/ml.

In some aspects, the present invention provides compositions and methods for administering oxybutynin to a subject such that the mean AUC ratio of oxybutynin to an oxybutynin metabolite is about 0.5:1 to about 5:1. In some aspects, the ratio is from about 0.5:1 to about 4:1; in some other aspects, the ratio is from about 1:1 to about 5:1; in yet other aspects, the ratio is from about 0.8:1 to about 2.5:1; in yet some other aspects, the ratio is from about 0.8:1 to about 1.5:1. In all the above aspects, the metabolite may be N-desethyloxybutynin.

Another way of characterizing the method of the present invention is by specifying particular plasma concentrations for oxybutynin and metabolite concentrations at certain time intervals following treatment initiation. Therefore, in one aspect, oxybutynin plasma concentrations are below about 2.0 ng/ml at about 6 hours after oxybutynin treatment initiation. In another aspect, the metabolite plasma concentrations are also below about 2.0 ng/ml at about 6 hours after treatment initiation.

In yet another aspect, oxybutynin and its metabolite plasma concentrations are below about 8 ng/ml at about 24 hours after initial oxybutynin administration. Further, mean steady state oxybutynin and its metabolite plasma-concentrations are below about 8 ng/ml for the duration of oxybutynin treatment.

In one aspect, the mean peak and mean AUC for (R)-N-desethyloxybutynin are about equal to or less than the mean peak, and mean AUC for (S)-N-desethyloxybutynin. In another aspect, the mean AUC ratio of (R)-N-desethyloxybutynin to (S)-N-desethyloxybutynin is about 0.9:1. In yet another aspect, the mean peak and mean AUC for (R)-oxybutynin are approximately equal to (R)-N-desethyloxybutynin. In another aspect, the ratio of (R)-N-desethyloxybutynin to (S)-N-desethyloxybutynin is about 1:1.

In an additional aspect, (R)-N-desethyloxybutynin has a mean peak plasma concentration of less than about 4 ng/mL. In another aspect, (R)-N-desethyloxybutynin has a mean peak plasma concentration between about 0.25 to about 4 nm/ml, and about 1.5 ng/ml.

In a one aspect, (R)-N-desethyloxybutynin has a mean AUC of about 100 ng×hr/ml. In another aspect, (R)-N-desethyloxybutynin has a mean AUC from about 30 ng×hr/ml to about 170 ng×hr/ml.

In yet another aspect, the plasma concentration of (R)-N-desethyloxybutynin is below about 1 ng/ml at about 6 hours after initiation of oxybutynin administration. In a further aspect, the plasma concentration of (R)-N-desethyloxybutynin is below about 2 ng/ml at about 24 hours after initiation of oxybutynin administration.

Therapeutic oxybutynin plasma concentrations vary based on the severity of incontinence. Generally, therapeutic results may be obtained from oxybutynin plasma concentrations as low as 0.5 ng/ml. Therapeutic blood levels may be achieved using the method of the present invention in as little as 3 hours after treatment initiation, with peak oxybutynin plasma concentrations being reached in about 24 hours. However, these general parameters are not limitations on the way in which the desired plasma levels may be achieved. Different delivery methods, rates, and amounts may be used to effect the desired plasma concentrations by employing a formulation which produces different parameters.

5) Composition Aspects

Any pharmaceutically acceptable compositions and methods for administering such compositions may be used for achieving the desired aspects of this invention. For example, oral and non-oral compositions and methods of administration can be used. Non-oral compositions and methods of administration include parenteral, implantation, inhalation, and transdermal compositions and methods.

Oral compositions and administrations can comprise of slow-release compositions that are designed to mimic the non-oral compositions and administrations that are specifically disclosed herein in terms of their pharmacokinetic attributes described above. One of ordinary skill in the art would readily understand how to formulate and administer such slow-release oral formulations. These formulations can take the form of a tablet, capsule, caplet, pellets, encapsulated pellets, etc., or a liquid formulation such as a solution or suspension. See, for example, U.S. Pat. No. 5,840,754, and WO 99/48494 which are incorporated by reference in their entirety.

Parenteral compositions and administrations may include intravenous, intra-arterial, intramuscular, intrathecal, subcutaneous, etc. These compositions can be prepared and administered to provide slow-release of oxybutynin to achieve the pharmacokinetic profile and therapeutic benefits described above. One specific example of preparing a depot-formulation for parenteral use is provided herein. General methods for preparing sustained delivery of drugs for parenteral use comprising microspheres are known in the art. See for example, U.S. Pat. Nos. 5,575,987, 5,759,583, 5,028,430, 4,959,217, and 4,652,441, hich are incorporated by reference in their entirety.

Implantation is a technique that is well-established to provide controlled release of drugs over a long period of time. Several subcutaneously implantable devices have been disclosed in the art. See for example, U.S. Pat. Nos. 5,985,305, 5,972,369, and 5,922,342, which are incorporated by reference in their entirety. By employing these general techniques, one of ordinary skill in the art can prepare and administer implantable oxybutynin compositions to achieve the pharmacokinetic and therapeutic benefits of this invention.

Examples of oxybutynin transdermal administration formulations include but are not limited to: 1) topical formulations such as ointments, lotions, gels, pastes, mousses, aerosols, and skin creams; 2) transdermal patches such as adhesive matrix patches and liquid reservoir systems. Other non-oral examples include transmucosal tablets such as buccal, or sublingual tablets or lozenges, and suppositories.

In addition to the desired amount of oxybutynin, transdermal oxybutynin formulations may also include a permeation enhancer, or mixture of permeation enhancers in order to increase the permeability of the skin to oxybutynin. A comprehensive index of permeation enhancers is disclosed by David W. Osborne and Jill J. Henke, in their internet publication entitled *Skin Penetration Enhancers Cited in the Technical Literature*, which may be found at the worldwide web address known as: pharmtech.com/technical/osborne/osborne.htm, which is incorporated by reference herein.

More particularly, permeation enhancers known to enhance the delivery of oxybutynin include but are not limited to: fatty acids, fatty acid esters, fatty alcohols, fatty acid esters of lactic acid or glycolic acid, glycerol tri-, di- and monoesters, triacetin, short chain alcohols, and mixtures thereof. Specific species or combinations of species may be selected from the above listed classes of compounds by one skilled in the art, in order to optimize enhancement of the particular oxybutynin composition employed.

The transdermal formulation of the present invention may take the form of an occlusive device, such as a transdermal patch. Such a transdermal patch may either be an adhesive matrix patch, a liquid reservoir system type patch, a buccal tablet, lozenge, or the like. Optional ingredients such as adhesives, excipients, backing films, etc, and the required amount of each will vary greatly depending upon the type of patch desired, and may be determined as needed by one ordinarily skilled in the art. Methods for preparing and administering the transdermal formulations with the above-described characteristics are known in the art. See, for example, U.S. Pat. Nos. 5,862,555, 5,762,953, and 5,152,997, which are incorporated by reference in their entirety.

However, these general parameters are not limitations on the way in which the desired plasma levels may be achieved. Different delivery methods, rates, and amounts may be used to effect the desired plasma levels by employing a formulation which produces different parameters.

EXAMPLES

The following examples of non-oral delivery formulations having a variety of oxybutynin containing compositions are provided to promote a more clear understanding of the possible combinations of the present invention, and are in no way meant as a limitation thereon.

Materials used in the present invention were obtained from specific sources which are provided as follows. Where the materials are available from a variety of commercial sources, no specific source has been provided. Oxybutynin free base was obtained from Ceres Chemical Co. Inc., White Plains, N.Y. (USA). The enantiomers of oxybutynin and namely, the (R)- and (S)-isomers were obtained from Sepracor. Sepracor, Marlborough, Mass. (USA).

Example 1

Preparation of Oxybutynin Adhesive Matrix Patch

The non-oral oxybutynin delivery devices used in the clinical study referred to above were 13 and/or 39 $cm^2$ transdermal adhesive matrix patches. A general method of preparing transdermal adhesive matrix patches is described by U.S. Pat. Nos. 5,227,169, and 5,212,199, which are incorporated by reference in their entirety. Following this general method, the oxybutynin patches of this invention were prepared as follows:

Oxybutynin free base, triacetin (Eastman Chemical Co., Kingsport, N.Y.) and 87-2888 acrylic copolymer adhesives (National Starch and Chemical Co., Bridgewater, N.J.) were mixed into a homogenous solution and coated at 6 mg/cm$^2$ (dried weight) onto a silicone treated polyester release liner (Rexham Release, Chicago, Ill.) using a two zone coating/drying/laminating oven (Kraemer Koating, Lakewood, N.J.) to provide a final oxybutynin adhesive matrix containing 15.4%, 9.0%, and 75.6% by weight oxybutynin, triacetin and acrylic copolymer adhesive, respectively. A fifty micron thick polyethylene backing film (3M, St. Paul, Minn.) was subsequently laminated onto the dried adhesive surface of the oxybutynin containing adhesive matrix and the final laminate structure was die cut to provide patches ranging in size from 13 cm$^2$ to 39 cm$^2$ patches.

Example 2

Preparation of Oxybutynin Biodegradable Microsphere Depot Injection

Biodegradable microspheres for effecting a sustained-release depot injection may be used to deliver oxybutynin in accordance with the method of the present invention. Microspheres were prepared by the following method:

12,000 molecular weight poly-d,l lactic acid ("PLA", Birmingham Polymers, Birmingham, Ala.) was dissolved into methylene chloride at a final concentration of 20% by weight. Oxybutynin free base was dissolved into the PLA solution at 4% by weight in the final solution. A water-jacketed reaction vessel (temperature controlled at 5 degrees Celsius) equipped with a true-bore stirrer fitted with a Teflon turbine impeller was charged with a de-ionized water containing 0.1% Tween 80.

The oxybutynin/PLA/methylene chloride solution was added drop wise into the reaction vessel and stirred to dispense the organic polymer phase within the aqueous solution as fine particles. The resultant suspension was filtered and washed once with de-ionized water and finally dried on a roto-evaporator to removed methylene chloride. The resultant microspheres can be injected either intramuscularly or subcutaneously to provide a prolonged systemic release of oxybutynin.

Example 3

Preparation of Topical Oxybutynin Formulation

Topically applied oxybutynin containing gel may be used to deliver oxybutynin in accordance with the method of the present invention. A general method of preparing a topical gel is known in the art. Following this general method, a topical gel comprising oxybutynin was prepared as follows:

95% ethanol (USP) was diluted with water (USP), glycerin (USP), and glycerol monooleate (Eastman Chemical, Kingsport N.Y.) to provide a final solution at ethanol/water/glycerin/glycerol monooleate percent ratios of 35/59/5/1, respectively. Oxybutynin free base was then dissolved into the above solution to a concentration of 10 mg/gram. The resultant solution was then gelled with 1% hydroxypropyl cellulose (Aqualon, Wilmington, Del.) to provide a final oxybutynin gel. One to two grams of the above gel is applied topically to approximately 200 cm$^2$ surface area on the chest, torso, and or arms to provide topical administration of oxybutynin.

Example 4

Clinical Study to the Determine the Pharmacokinetics of Oxybutynin, N-desethyloxybutynin and their Respective (R) and (S) Isomers following Oral administration of Racemic Oxybutynin in Comparison to Transdermally Administered Racemic Oxybutynin A clinical study in 16 healthy volunteers compared, in a cross-over fashion, the comparative plasma concentrations and pharmacokinetics of oxybutynin, N-desethyloxybutynin, and their respective (R)- and (S)-enantiomeric components.

Healthy volunteers were recruited from the local population and included men and women ranging in age from 19 to 45 years. Following a pre-study examination to confirm a healthy condition in all volunteers, each subject participated in 2 study periods during which the test medications, either a transdermal oxybutynin system applied for 4 days or a single 5 mg oral immediate-release dose of oxybutynin, were administered. Blood samples were collected periodically throughout the study periods. Plasma was harvested from the samples according to a standard method. The quantities of (R) and (S) oxybutynin and (R) and (S)N-desethyloxybutynin were measured in the plasma samples through the application of a validated mass spectrometric method coupled with liquid chromatographic separation of the individual constituents. A Perkin Elmer high performance liquid chromatographic pump was used in conjunction with a Chrom Tech AGP 150.2 chromatographic column. The mass spectrometry instrument was an API 300 operated in MRM scan mode with electrospray ionization. A linear response of the quantitation of the analytes was confirmed with standard solutions and the performance of the assay was controlled using quality control samples analyzed in conjunction with the study samples. The range of linearity was 0.5 to 75 ng/ml with linear correlation coefficients greater than 0.99 for all analytes.

FIGS. 1,2,3,6, and 7 show graphical displays of these data. In FIG. 1, oxybutynin and N-desethyloxybutynin plasma concentrations are shown following administration of the 5 mg immediate-release oral dosage oxybutynin hydrochloride tablets, Ditropan® Alza Corporation. These tablets were obtained commercially and can be obtained from various generic manufacturers. Plasma concentration is indicated on the vertical axis, and time is indicated on the horizontal axis. As can be seen, the plasma concentrations of N-desethyloxybutynin are significantly greater than oxybutynin plasma concentrations. The mean AUC ratio for N-desethyloxybutynin to oxybutynin is about 10:1.

Figure 3:
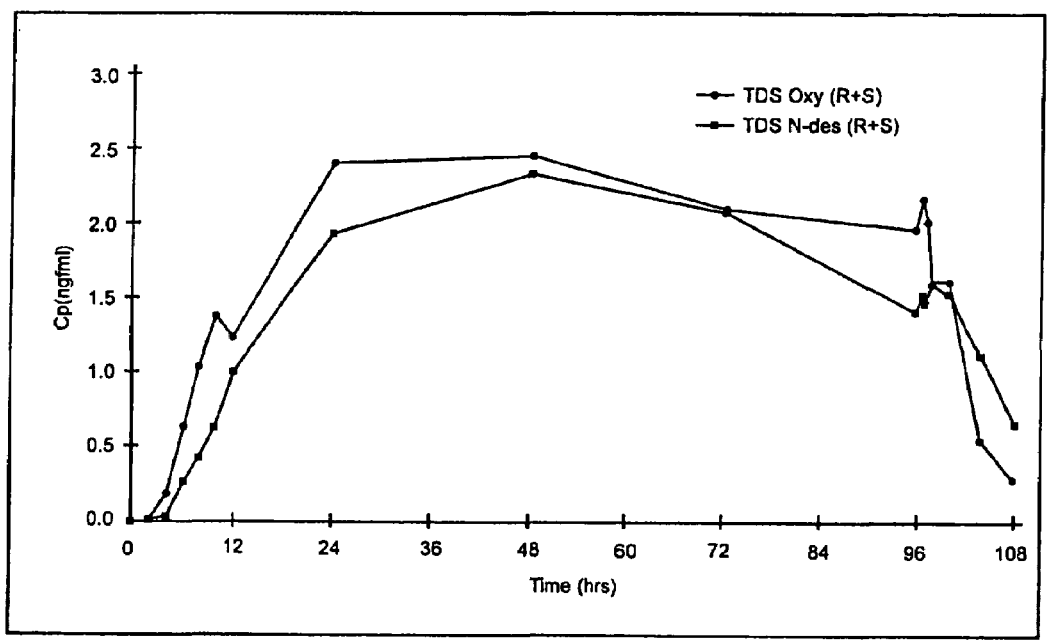
FIG. 3 is a graphical representation of total oxybutynin and N-desethyloxybutynin plasma concentrations measured upon transdermal administration according to the present invention, spanning a time from initial oxybutynin administration to 96 hours therefrom, and for an additional 12 hours following the removal of the transdermal system at 96 hours.

FIG. 3 illustrates the plasma concentration profiles for oxybutynin and N-desethyloxybutynin during and following application of the transdermal system. As can be seen, the N-desethyloxybutynin plasma concentrations for the adhesive matrix patch embodiment, fall well within the parameters prescribed by the present invention. The mean AUC ratio for N-desethyloxybutynin to oxybutynin is about 0.9:1 and the mean plasma concentrations for N-desethyloxybutynin are less than about 2.5 ng/ml.

FIGS. 6 and 7 illustrate the plasma concentrations of the individual isomers of oxybutynin and N-desethyloxybutynin as measured during the clinical trial described above. As can be seen in FIG. 6, oral administration of oxybutynin leads to relatively high concentrations of (R)-N-desethyloxybutynin. This active metabolite moiety is present in the greatest concentration, and is several times the concentration of both (R) and (S) oxybutynin. The mean ratio of AUC of (R)-N-desethyloxybutynin to (R)-oxybutynin is about 17:1 and the mean AUC ratio of (R)-N-desethyloxybutynin to (S)-N-desethyloxybutynin is about 1.5:1.

Following application of the transdermal oxybutynin system, the mean AUC ratio of the active moieties, (R)-N-desethyloxybutynin to (R)-oxybutynin, is about 1:1, substantially lower than following oral administration. Additionally, the mean AUC ratio of (R)-N-desethyloxybutynin to (S)-N-desethyloxybutynin is about 0.9:1, consistent with substantially lower metabolic first pass conversion of the active (R)-oxybutynin to (R)-N-desethyloxybutynin. The mean AUC ratio of (R)- to (S)-oxybutynin is about 0.7:1, similar to that present following oral administration.

The lower overall amount of oxybutynin delivered during transdermal delivery of oxybutynin was estimated based on the residual amount of oxybutynin remaining in the transdermal system after the 4-day application period subtracted from the amount determined in unused transdermal systems. The mean amount delivered over 4 days was about 12 mg or an average of about 3 mg/day. The oral dose of oxybutynin administered in the study was 5 mg, a dose that may be administered every 12 hours, or two times daily, during therapeutic use of the product. This allows a comparison of a dose of about 5 mg every 12 hours for oral treatment compared to about 1.5 mg every 12 hours for transdermal treatment.

In summary, the pharmacokinetics of transdermal, non-oral, oxybutynin administration illustrate the aspects of the invention with regard to a sustained, slower rate of administration of oxybutynin and a lower dose or overall amount of oxybutynin administered.

Example 5

Comparative Analysis of Therapeutic Efficacy and Incidence and Severity of Anticholinergic Side Effects, Primarily Dry Mouth, of Conventional Oral Tablet Formulation and Transdermal Formulation of the Present Invention A clinical study of the efficacy and incidence of side effects was conducted in 72 patients with overactive bladder. These patients were recruited by independent clinical investigators located in various regions of the U.S.A. Approximately half of the patients were administered oxybutynin hydrochloride in an immediate-release oral dosage formulation. The remaining patients were administered oxybutynin using in each case one or more 13 $cm^2$ oxybutynin containing transdermal adhesive matrix patches. In each of these treatment groups, the medications were blinded by the concomitant administration of matching placebo forms of the treatments. In the case of active oral treatment, the patients applied placebo transdermal systems that contained all ingredients of the active transdermal system with the exception of the active drug oxybutynin. In like fashion, the active transdermal treatment group received matching oral formulations without the active oxybutynin constituent. In this study, the patients included both men and women, with the majority being women with an average age of 63–64 years. All patients had a history of urinary incontinence associated with overactive bladder and demonstrated a mean of at least 3 incontinent episodes per day during a washout period during which no medical therapy for incontinence was used.

Therapeutic efficacy was based on the mean number of incontinent episodes experienced per day as derived from a multiple-day patient urinary diary. The data are displayed graphically in FIG. 4.

As can be seen, the number of incontinent episodes for those individuals treated by the non-oral method of the present invention is nearly identical to the number for those treated with the oral formulation. This indicates clearly that the present methods and compositions provide for a therapeutically effective treatment for urinary incontinence and overactive bladder that is comparable to the conventional oral formulation, such as a 5 mg oral oxybutynin tablet. Incidence and/or severity of adverse drug experience was also compared between the conventional oral tablet formulation of oxybutynin administered as above and the transdermal formulation. Anticholinergic adverse experience, such as the incidence and severity of dry mouth, was used as an indicator of the adverse experience that can be associated with the administration of either formulation and represents an anticholinergic side effect. The clinical study participants were asked to report this experience according to a standardized questionnaire. The data derived from the questionnaire are displayed graphically in FIG. 5. The percentage of participants reporting dry mouth is indicated on the vertical axis, and the severity of the dry mouth is indicated on the horizontal axis.

As can be seen, only 6% of the participants who received the oral form reported no dry mouth effects. Conversely, 94% of these participants reported experiencing some dry mouth. By contrast, 62% of the participants who were treated with the 13 $cm^2$ transdermal adhesive matrix patches reported no dry mouth effects. Therefore, only 38% of these participants reported experiencing some dry mouth. Therefore, the clinical data shows that matrix patch embodiment of the method of the present invention, provides a treatment for overactive bladder which achieves nearly identical therapeutic effectiveness as an oral form, while significantly minimizing the incidence and or severity of adverse experiences associated with oxybutynin administration.

FIG. 7 shows that the (R)-N-desethyloxybutynin concentrations are lower than the (S)-N-desethyloxybutynin concentrations, and further, the concentrations of (R)-oxybutynin increase slowly and are maintained at an approximately constant level throughout the patch application time period. The reduced plasma concentrations of (R)-N-desethyloxybutynin appears to have contributed to the minimization of the incidence and severity of adverse drug experiences such as dry mouth, while the plasma concentrations of (R)-oxybutynin retain the therapeutic effectiveness of the treatment, as shown by FIGS. 4 and 5.

It is to be understood that the above-described compositions and modes of application are only illustrative of preferred embodiments of the present invention. Numerous modifications and alternative arrangements may be devised by those skilled in the art without departing from the spirit and scope of the present invention and the appended claims are intended to cover such modifications and arrangements.

Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method of treating with oxybutynin a subject having overactive bladder, while minimizing an anticholinergic or antimuscarinic adverse drug experience associated with said oxybutynin treatment therapy comprising the step of:
  a administering a transmucosal formulation, comprising oxybutynin to a subject to provide a plasma area under the curve (AUC) ratio of oxybutynin to an oxybutynin metabolite of from about 0.5:1 to about 5:1, wherein the transmucosal formulation optionally includes a permeation enhancer, and wherein the transmucosal formulation is selected from the group consisting of a buccal tablet, a sublingual tablet, or an adhesive film.

2. The method of claim 1, wherein the AUC ratio of oxybutynin to an oxybutynin metabolite is from about 1:1 to about 5:1.

3. The method of claim 1, wherein the AUC ratio of oxybutynin to an oxybutynin metabolite is from about 0.8:1 to about 1.5:1.

4. The method of claim 1, wherein the oxybutynin in the plasma is (R)-oxybutynin, (S)-oxybutynin, or a combination thereof.

5. The method of claim 4, wherein the metabolite of oxybutynin is N-desethyloxybutynin.

6. The method of claim 5, wherein the N-desethyloxybutynin is (R)-N-desethyloxybutynin, (S)-N-desethyloxybutynin or a combination thereof.

7. The method of claim 4, wherein the AUC ratio of (R)-oxybutynin to (S)-oxybutynin is about 0.7:1.

8. The method of claim 6, wherein the AUC ratio of (R)-N-desethyloxybutynin to (R)-oxybutynin is from about 0.4:1 to about 1.6:1.

9. The method of claim 8, wherein the AUC ratio of (R)-N-desethyloxybutynin to (R)-oxybutynin is about 1:1.

10. The method of claim 6, wherein the AUC ratio of (R)-N-desethyloxybutynin to (S)-N-desethyloxybutynin is from about 0.5:1 to about 1.3:1.

11. The method of claim 10, wherein the AUC ratio of (R)-N-desethyloxybutynin to (S)-N-desethyloxybutynin is about 0.9:1.

12. The method of claim 1, wherein a metabolite plasma concentration reaches a peak plasma value of less than about 8 ng/ml.

13. The method of claim 1, wherein a metabolite plasma concentration reaches a peak value of less than about 5 ng/ml.

14. The method of claim 1, wherein the adverse drug experience is an experience selected from the group consisting of: gastrointestinal/genitourinary, nervous system, cardiovascular, dermatological, and opthalmic experiences, or a combination thereof.

15. The method of claim 1, where the permeation enhancer is a member selected from the group consisting essentially of: fatty acids, fatty acid esters, fatty alcohols, fatty acid esters of lactic acid or glycolic acid, glycerol triesters, glycerol diesters, glycerol monoesters, triacetin, short chain alcohols, and mixtures thereof.

16. The method of claim 15, wherein the permeation enhancer is triacetin.

17. The method of claim 1, wherein the oxybutynin is a mixture of R-oxybutynin and S-oxybutynin.

18. The method of claim 1, wherein the oxybutynin is R-oxybutynin.

19. The method of claim 1, wherein the oxybutynin is S-oxybutynin.

20. The method of claim 1, wherein the metabolite is N-desethyloxybutynin and a reaches a peak plasma concentration of N-desethyloxybutynin about 0.5 ng/ml to about 8 ng/ml.

21. The method of claim 1, wherein the metabolite is N-desethyloxybutynin and a reaches a peak plasma concentration of N-desethyloxybutynin less than about 5 ng/ml.

22. The method of claim 1, wherein the metabolite is N-desethyloxybutynin and a reaches a peak plasma concentration of N-desethyloxybutynin from about 1.0 ng/ml to about 3 ng/ml.

23. The method of claim 1, wherein the metabolite is N-desethyloxybutynin and the N-desethyloxybutynin AUC does not exceed the oxybutynin AUC by more than a ratio of about 2:1.

24. The method of claim 1, wherein the metabolite is N-desethyloxybutynin and a has a peak plasma concentration of N-desethyloxybutynin 3 ng/ml.

25. The method of claim 1, wherein the metabolite is N-desethyloxybutynin and the AUC ratio of oxybutynin to N-desethyloxybutynin is from about 0.5:1 to about 4:1.

26. The method of claim 1, wherein the metabolite is N-desethyloxybutynin and the AUC ratio of oxybutynin to N-desethyloxybutynin is from about 1:1 to 5:1.

27. The method of claim 1, wherein the metabolite is N-desethyloxybutynin and the AUC ratio of oxybutynin to N-desethyloxybutynin is from about 0.8:1 to about 2.5:1.

28. The method of claim 3, wherein the metabolite is N-desethyloxybutynin.

29. The method of claim 1, wherein oxybutynin has plasma concentrations about 2.0 ng/ml at about 6 hours after administration.

30. The method of claim 1, wherein the metabolite is N-desethyloxybutynin and the N-desethyloxybutynin has plasma concentrations about 2.0 ng/ml at about 6 hours after administration.

31. The method of claim 1, wherein the metabolite is N-desethyloxybutynin, and oxybutynin and N-desethyloxybutynin have plasma concentrations about 8 ng/ml at about 24 hours after initial administration.

32. The method of claim 1, wherein the metabolite is N-desethyloxybutynin and at steady state, the oxybutynin and N-desethyloxybutynin have plasma concentrations below about 8 ng/ml for the duration of administration.

33. The method of claim 32, wherein the duration of administration is from about 24 to about 96 hours.

34. The method of claim 1, wherein the transmucosal formulation is administered for a duration of from about 24 to about 96 hours.

35. The method of claim 10, wherein a peak plasma concentration and AUC for (R)-N-desethyloxybutynin are about equal to or less than peak plasma concentration and AUC for (S)-N-desethyloxybutynin.

36. The method of claim 8, wherein a peak plasma concentration and AUC for (R)-oxybutynin are approximately equal to peak plasma concentration and AUC for (R)-N-desethyloxybutynin.

37. The method of claim 6, wherein (R)-N-desethyloxybutynin has a peak plasma concentration of less than about 4 ng/mL.

38. The method of claim 6, wherein (R)-N-desethyloxybutynin has a peak plasma concentration between about 0.25 ng/ml to about 4 ng/ml.

39. The method of claim 6, wherein (R)-N-desethyloxybutynin has a peak plasma concentration of about 1.5 ng/ml.

40. The method of claim 6, wherein (R)-N-desethyloxybutynin has an AUC of about 100 ng×hr/ml.

41. The method of claim 6, wherein (R)-N-desethyloxybutynin has an AUC of from about 30 ng×hr/ml to about 170 ng×hr/ml.

42. The method of claim 6, wherein (R)-N-desethyloxybutynin plasma concentration is below about 1 ng/ml at about 6 hours after initiation of administration.

43. The method of claim 6, wherein (R)-N-desethyloxybutynin plasma concentration is below about 2 ng/ml at about 24 hours after initiation of administration.

* * * * *